United States Patent [19]

Mathewes

[11] Patent Number: 4,501,162
[45] Date of Patent: Feb. 26, 1985

[54] SAMPLE-TAKING APPARATUS FOR A CONTAINER, CONTAINING A BULK MATERIAL FEED

[75] Inventor: Wolfgang Mathewes, Giessen, Fed. Rep. of Germany

[73] Assignee: Kraftwerk Union Aktiengesellschaft, Mülheim, Fed. Rep. of Germany

[21] Appl. No.: 468,567

[22] Filed: Feb. 22, 1983

[30] Foreign Application Priority Data

Feb. 22, 1982 [DE] Fed. Rep. of Germany ....... 3206323

[51] Int. Cl.³ .............................................. G01N 1/14
[52] U.S. Cl. ................................. 73/863.83; 222/413
[58] Field of Search ........... 73/863.81, 863.82, 863.83, 73/863.84, 863.85, 863.86; 222/412, 413; 55/270, 390; 210/85, 92

[56] References Cited

U.S. PATENT DOCUMENTS 2,056,239 10/1936 Walter ................................. 222/413
3,206,981 9/1965 Jameson ........................... 73/863.83
3,279,259 10/1966 Haley ................................ 73/863.83

FOREIGN PATENT DOCUMENTS 2421828 12/1979 France .

Primary Examiner—S. Clement Swisher
Attorney, Agent, or Firm—Herbert L. Lerner; Laurence A. Greenberg

[57] ABSTRACT

Sample-taking apparatus, includes a container for bulk material feed, the container having an upper cover region, a lower discharge region and a side wall having a discharge opening formed therein, the bulk material feed flowing at least discontinuously from the upper cover region to the lower discharge region of the container, an exposed sample-taking worm being attached to the side wall and projecting through the discharge opening into the feed for conveying bulk material samples from the feed by rotating, a rotary drive connected to the sample-taking worm, and a collecting device integral with the container, the worm having a shaft with an end, at least the end being immersed in the feed, the worm having worm threads formed thereon with surfaces forming an imaginary surface of projection extended normal to the worm shaft, the worm thread surfaces forming worm segments with increasingly smaller conveying surfaces as seen in direction toward increasing depth of immersion of the worm into the feed, during sample-taking in a quasi-stationary condition of the feed, the worm threads accumulating layered hollow cylindrical bulk material segments between the worm threads in subsets corresponding to worm segments from any one of the worm threads having a given spiral height to an adjacent one of the worm threads having a larger spiral height as seen in direction from the end of the shaft to the discharge opening, the subsets being representative of the bulk material of the respective segments of the worm.

20 Claims, 10 Drawing Figures

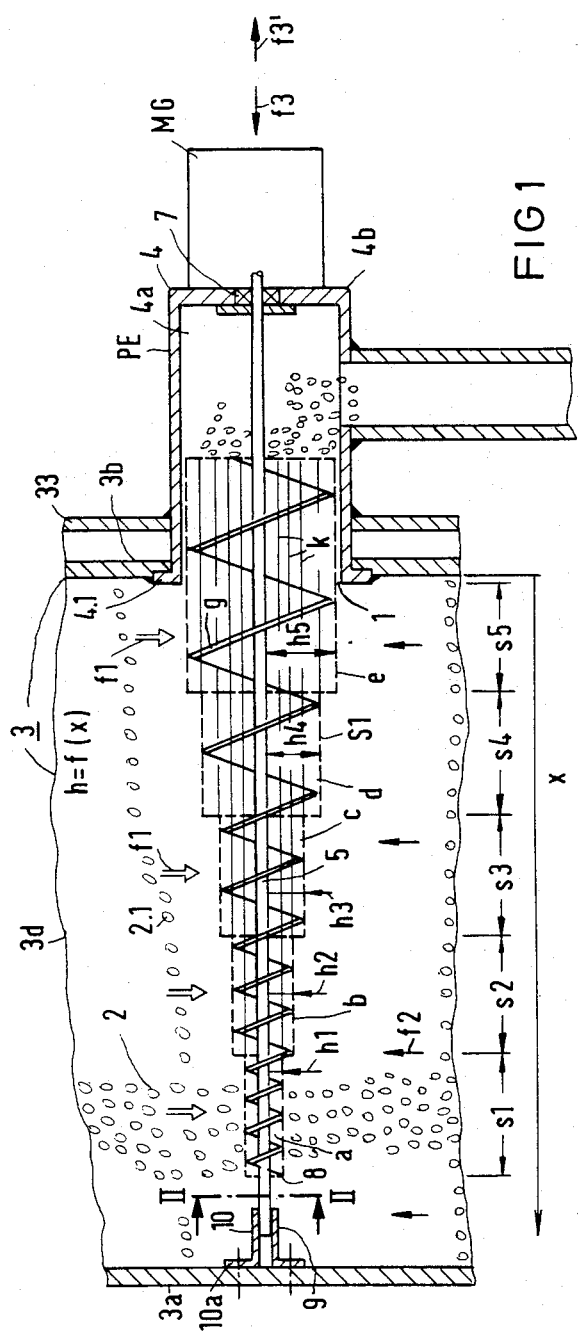
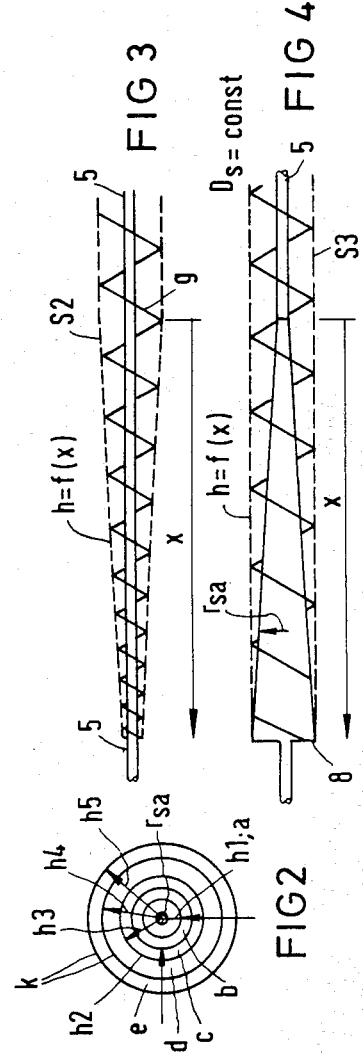

SAMPLE-TAKING APPARATUS FOR A CONTAINER, CONTAINING A BULK MATERIAL FEED

The invention relates to a sample-taking apparatus for a container containing bulk material feed which flows through the container at least discontinuously from top to bottom, with feeding of the bulk material from the cover side and with a discharge at the bottom, an uncovered sample-taking worm being fastened to the container wall and projecting through a discharge opening into the feed, a rotary drive and a collecting device into which the sample-taking worm conveys bulk material samples from the feed by rotating.

Such bulk material feeds exist in many forms in the art, for example, they can be feed, fertilizer or grain silos, wherein granular substances flow through discontinuously from top to bottom, in containers corresponding to those in U.S. Pat. Nos. 3,472,079 and 3,279,259 and in German Patent DE-PS No. 219 819. The bulk material feed can also be an ion exchanger, in which case the ionic exchanging mass in a container likewise flows discontinuously from top to bottom, and the fluid to be conditioned or the water to be prepared respectively flows through the feed from bottom to top, preferably in a counterflow. Of special importance are sample-taking apparatus for a bulk material filter, particularly for so-called activated carbon filters in nuclear power stations. In this case, the feed is formed of a filter bed of activated carbon bodies; the filter mass travels through the filter container discontinuously from top to bottom and flows through from the exhaust gas to be cleaned, preferably likewise in a counterflow, although a cross flow can also be used. Ultimately, without claiming to be complete, particle heat exchangers are referred to as so-called pebble heaters, in which the heat exchanging mass is formed of ceramic bodies or steel balls, which flow from top to bottom at least discontinuously in the container of the heat exchanger, and can flow through from the heat exchanging gas from bottom to top, preferably in a counterflow. However, it can also be in a cross, direct, or cross-counterflow.

For all of the above-mentioned known systems of bulk material feed, a problem of sample-taking exists, which occurs during operation and should cover as representative a cross section of the bulk material feed as possible, without the desired flow of the bulk material, possibly in plane parallel layers or according to a type of piston movement, respectively, being influenced in the direction of an undesired core flow. In the case of an undesired core flow, preferred flow zones of the bulk material occur at the cost of other zones, which then remain practically inoperative, and therefore are also described as dead zones. These points of view have special meaning for filter technology, and especially for adsorption filters in technical nuclear installations, wherein the function of the filter in continuous operation must be maintained under all circumstances and a so-called filter breakthrough must be avoided, while specific limiting values, such as minimal remaining contents of radioactive iodine (split iodine) in the exhaust air must be guaranteed below a limiting value.

Such adsorption filters, which specifically work with activated carbon as a filter mass, must have separate grades of at least 99%. Details of the special functions of the adsorption filters in nuclear technology are given in German Patent DE-PS No. 26 25 275.

The sample-taking apparatus, taken from the above-mentioned three patent disclosures from which the concept according to the invention is derived, are not suitable for taking a representative bulk material cross section from the bulk material feed, which is relatively stationary at the moment of sample-taking, without disturbing the piston flow, while the sample-taking worms shown therein, with constant spiral height, have the attribute of conveying the bulk material only from the immersion end thereof to the discharge outlet. Relatively or quasi-stationary feed in this case is understood to mean that the bulk material is resting. However, in the case of sample-taking, the bulk material can slide down from the top into hollow spaces, which are caused by sample-taking, wherein sliding down in layers that are as plane parallel to each other as possible is desired, so that the cross-sectional view of the feed is not disturbed. In other words: in a bulk material feed formed of flowable particles, which is found in a relatively stationary or quasi-stationary condition, respectively, the particles can slide down during sample-taking, which in this particular case refers to the present invention. This means that in the case of continuous flow of bulk material feed, as far as the invention is concerned, a quasi-stationary condition must be present for sample-taking. In a continous top to bottom flow of bulk material feed, in the case of sample-taking with a sample-taking worm, which has the same spiral height over its length, a conveyance of the particles only from the worm end toward the discharge outlet is avoided. However, a representative sample-taking over the cross section is also not obtainable, while the particles from the feed cross section, which are respectively situated closest to the discharge outlet predominate and therefore the rest of the cross-sectional zones in the sample are taken less into account, or not at all.

It is accordingly an object of the invention to provide a sample-taking apparatus for a container, containing a bulk material feed, which overcomes the hereinafore-mentioned disadvantages of the heretofore-known devices of this general type.

With the foregoing and other objects in view there is provided, in accordance with invention, a sample-taking apparatus, comprising a container for bulk material feed, the container having an upper cover region, a lower discharge region and a side wall having a discharge opening formed therein, the bulk material feed flowing at least discontinuously from the upper cover region to the lower discharge region of the container, an exposed or uncovered sample-taking worm being attached to the side wall and projecting through the discharge opening into the feed for conveying bulk material samples from the feed by rotating, a rotary drive connected to the sample-taking worm, and a collecting device integral with the container, the worm having a shaft with an end, at least the end being immersed in the feed, the worm having worm threads formed thereon with surfaces forming an imaginary surface of projection extended normal to the worm shaft, the worm thread surfaces forming worm segments with increasingly smaller conveying surfaces as seen in direction toward increasing depth of immersion of the worm into the feed, during sample-taking in a quasi-stationary condition of the feed, the worm threads accumulating layered hollow cylindrical bulk material segments between the worm threads in subsets corresponding to worm segments from any one of the worm threads having a given spiral height to an adjacent one of said worm threads having a larger height as seen in direction from the end of the shaft to the discharge opening, the subsets being representative of the bulk material of the respective segments of the worm.

With this apparatus, it is possible to take samples at any level from the bulk material feed, which are representative of the cross section of the feed at the particular position. In this case, the plane parallel layering or the so-called piston flow of the bulk material feed in this cross-sectional zone is not considerably disturbed. In other words: each of the proposed sample-taking columns perpendicular to the worm shaft should be taken in equal amounts of particles, so that when the sample-taking covers a partial cross section or the entire cross section, for a given column content, the layering of the feed moves parallel thereto by itself, and also in the case of discharging on the bottom and/or in the case of feeding from the cover side of the bulk material, an analogous parallel movement of the bulk material occurs as a piston flow.

In accordance with another feature of the invention, the conveying surfaces of the worm segments steadily decrease in size as seen in direction toward increasing depth of immersion of the worm into the feed.

In accordance with a further feature of the invention, the sample-taking worm has a substantially conically tapered outer contour from the discharge opening to the end of the shaft, and the shaft is cylindrical.

In accordance with an additional feature of the invention, the sample-taking worm has a substantially conically tapered outer contour from the discharge opening to the end of the shaft, and the shaft is also conically tapered toward the end of the shaft and is more pointed than the outer contour of the worm.

In accordance with again another feature of the invention, the spiral height of the worm threads from the shaft to the outer periphery of the worm determining the size of the respective conveying surfaces, decreases substantially linearly as seen in direction toward the shaft end along the shaft.

In accordance with again a further feature of the invention, the three smallest of the spiral heights of the worm threads are decreased over-proportionately as compared to the others of the worm threads.

In accordance with again an added feature of the invention, the spiral height of the worm threads is given another correction function, in which case the curve thereof falls off substantially linearly from the largest to the smallest spiral height, and the spiral height is increased in vicinity of the first two threads toward the discharge opening and is decreased in vicinity of the third and fourth threads.

In accordance with again an additional feature of the invention, the bulk material feed is a bed of a bulk material filter, through which fluids to be cleaned flow in a given direction, the filter bed having respective opposite feeding and discharge filter sides, the sample-taking worm projecting into the filter bed substantially perpendicularly to the fluid flow direction.

In accordance with yet another feature of the invention, the bulk material feed is an adsorption filter, especially an activated carbon filter, with a discontinuous flow of adsorption means from top to bottom and with a continuous counterflow of gases to be filtered from the bottom to the top, at least one sample-taking worm projecting in the horizontal direction into the filter bed.

In accordance with yet a further feature of the invention, the bulk material filter has a substantially rectangular cross section, the filter container has shell surface, and the sample-taking worm projects into the filter bed with the shaft being parallel to the surfaces of the container.

In accordance with yet an added feature of the invention, there is provided at least one additional sample-taking worm, several, i.e. at least two, of the worms being disposed at one of the surfaces of the container at different heights relative to the bulk material filter and laterally staggered with respect to each other.

In accordance with yet an additional feature of the invention, the sample-taking worms include at least three sloping worms.

In accordance with still a further feature of the invention, the shaft has another end projecting outside the container wall, and including a worm tube disposed on the other end and a collecting device connected to the worm tube, the collecting device including a sluice having, especially, a sight glass-shaped sluice pot, shut-off devices connected upstream and downstream of the sluice pot, a discharge pipe connected to the sluice, and a collecting container connected to the discharge pipe.

In accordance with still another feature of the invention, the collecting container is a protective bag having an opening formed therein defining a rim, and including a fluted protective bag ring at which the discharge pipe terminates, the ring being gas-tightly clamped to the rim.

In accordance with still an added feature of the invention, there are provided first shut-off devices respectively connected to a plurality of the sample-taking worms, discharge pipes respectively connected downstream of the first shut-off devices, a common inclined collecting pipe into which the discharge pipes are connected for discharging, a sight glass extension connected to the common collecting pipe, a second shut-off device connected to the sight glass extension, and a protective bag gas-tightly clamped to the collecting pipe through the extension and second shut-off device.

In accordance with still an additional feature of the invention, there is provided at least one additional container having sample-taking worms and discharge pipes, the discharge pipes of the sample-taking worms of at least two mutually adjoining containers being connected to collecting pipes.

In accordance with another feature of the invention, there is provided a worm tube disposed on the worm at an end of the shaft opposite the first-mentioned end, a support rod fastened to the container wall opposite the worm tube, and a pivot bearing being supported by the support rod and being in alignment with and pivotably connected to the first-mentioned end of the shaft.

In accordance with a further feature of the invention, the sample-taking worm has a constant outer diameter throughout the length thereof, and the shaft has a diameter being increased as seen in direction from the discharge opening to the end of the shaft.

In accordance with an added feature of the invention, the size of the conveying surfaces and the spiral height of the threads of the worm decrease as seen in direction toward increasing immersion of the worm in the feed, according to a type of step curve.

In accordance with a concomitant feature of the invention, the bulk material feed is an adsorption filter, especially an activated carbon filter, with a discontinuous flow of adsorption means from top to bottom and with a continuous counter or cross flow of gases to be filtered in a given direction through the filter bed, at least one sample-taking worm projecting into the filter bed across the gas flow direction.

Through the special construction, and particularly the conicity of the sample-taking worm, besides the transport of a bulk material core segment amount (meaning the amount which is conveyed from the outer worm threads, on the average having the smallest spiral height) between the individual worm spirals from the immersion end in the direction toward the discharge opening, from one spiral height to the next larger spiral height, respectively, other bulk material subsets are obtained in addition to the core amount. In this case, reference is made to the level in a bulk bed, into which the sample-taking worm projects, and a sample-taking amount in the form of an elongated content in a level perpendicular thereto is taken from the bulk material feed (cross-sectional sample). The conveyed bulk material, is filled up by bulk material which slides down from the top due to gravity between the spirals or the worm spirals of the sample-taking worm, respectively.

An especially important application of a bulk material filter with a worm projecting into the filter bed perpendicularly to the fluid flow direction, is an adsorption filter, particularly an activated carbon filter, like those frequently used in nuclear technology installations or overall in similar installations, where air or exhaust of noxious gases or aerosols must be filtered. In this way, a discontinuous flow of the adsorption means occurs from top to bottom and a continuous flow (apart from a servicing pause) of the gases to be filtered in a counter flow occurs from bottom to top. In the case of the use of such adsorption filters, at least one sample-taking worm projects in the horizontal direction into the filter bed. In this case, the conveyed activated carbon is also filled up by activated carbon which slides down from the top into the spirals of the sample-taking worm due to gravity. The new activated carbon stored in the worm spaces, then again takes part in the adsorption process, like all the other carbon granules, which are situated at the same height of the filter bed, but are outside of the sample-taking worm.

In the normal operation and also during sample-taking, the air to be filtered on the way through the filter bed also flows around the contour of the core and the spiral of the sample-taking worm. It is thus guaranteed that the activated carbon, which is also stored between the spirals, during the loading procedure, can participate in the adsorption process and therefore in the loading procedure. The adsorption means and the activated carbon, respectively, can only be taken from levels at the same loading progress, particularly in the case of an adsorption filter of the afore-described construction. No misleading information occurs and it can be established that the actual loading condition for the given sample-taking level according to the samples taken, depends on the fact that spent filter material can be discharged from the bottom and unused material can be brought from the top for sliding down, or this procedure can still be delayed. The layering of the filter bed is maintained in layers that are plane parallel to each other and turbulent core flow is avoided.

Other features which are considered as characteristic for the invention are set forth in the appended claims.

Although the invention is illustrated and described herein as embodied in a sample-taking apparatus for a container containing a bulk material feed, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings, in which:

FIG. 1 is a fragmentary, diagrammatic, cross-sectional view of a sample-taking apparatus, which projects through the side wall of a container into a bulk material feed with a sample-taking worm or screw shaft conveyor, the representation not being true to scale for a better understanding;

FIG. 2 is a partially cross-sectional view taken in the longitudinal direction of the sample-taking worm, along the line II—II in FIG. 1, in the direction of the arrows;

FIG. 3 is a fragmentary, elevational view of a section of a sample-taking worm, in which the outer contour, contrary to FIG. 1, is not step-shaped, but is continuously conically tapered, the worm core being cylindrical as in FIG. 1 with the same diameter over the length of the screw shaft;

FIG. 4 is a view similar to FIG. 3 of a third embodiment of a sample-taking worm, in which the covering over the length thereof has a constant diameter, against which the core diameter increases from the worm at the outer bulk material, beginning at the end of the worm at the inner bulk material;

Figure 5:
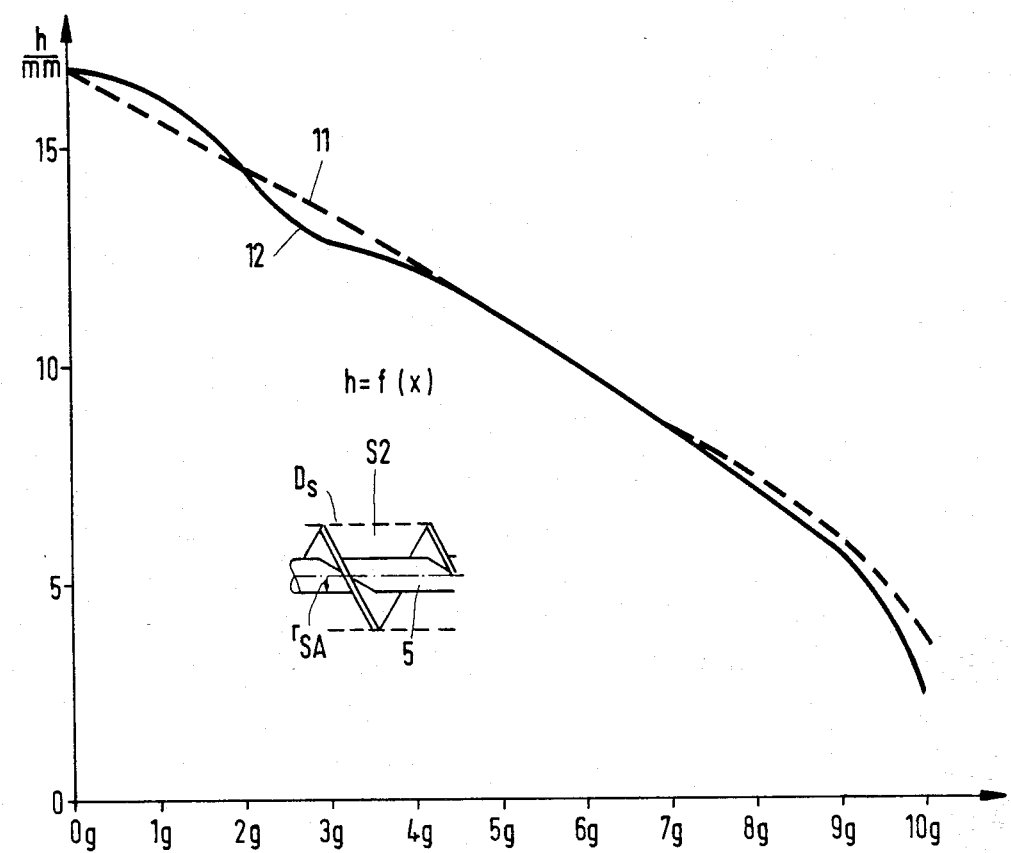
Figure 6:
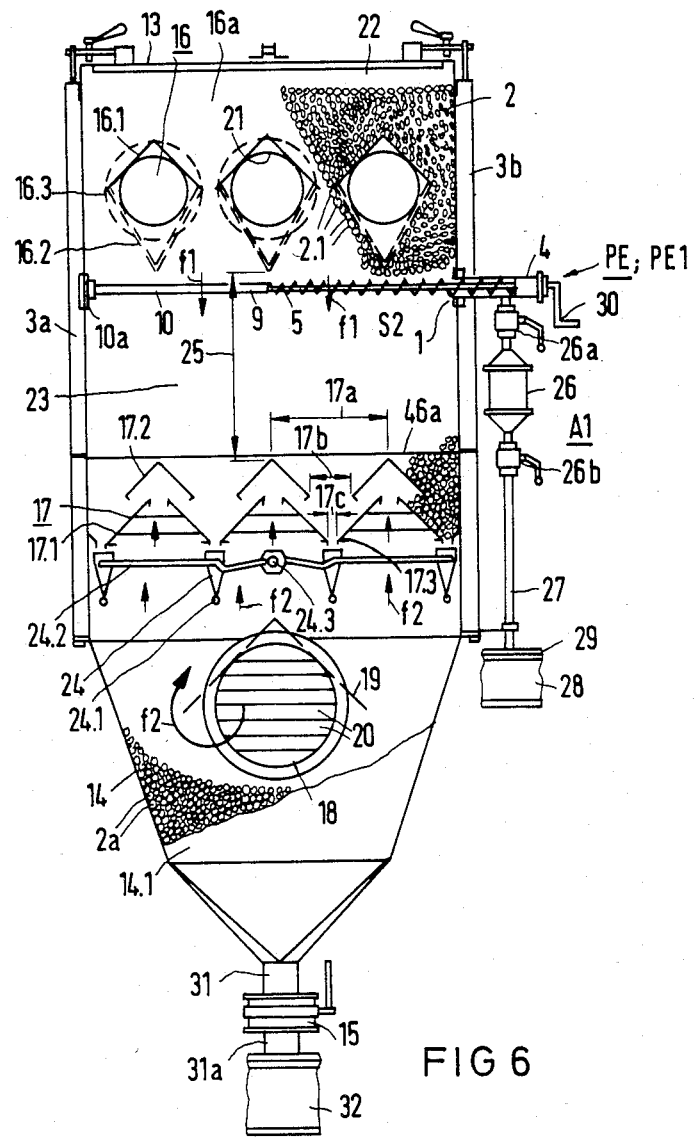
Figure 7:
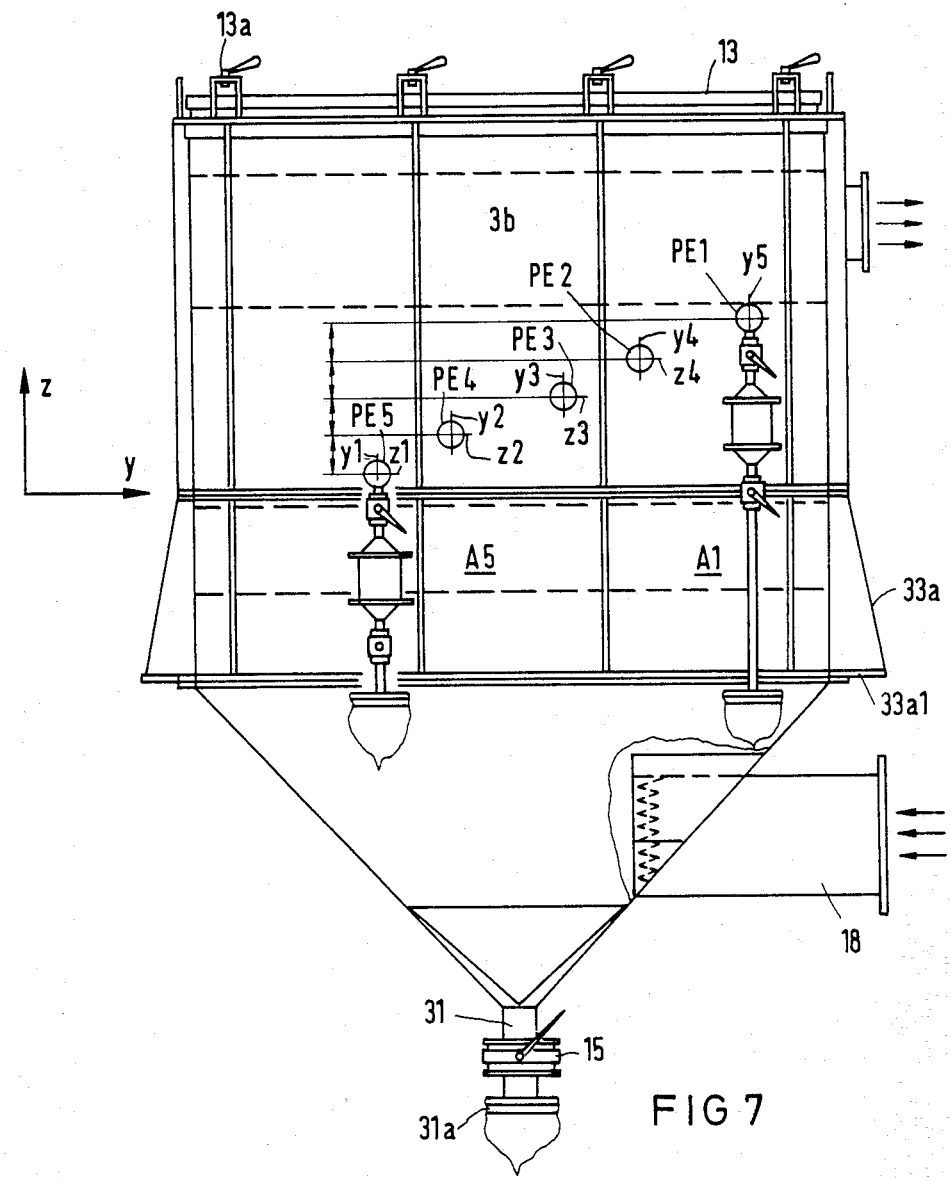
Figure 8:
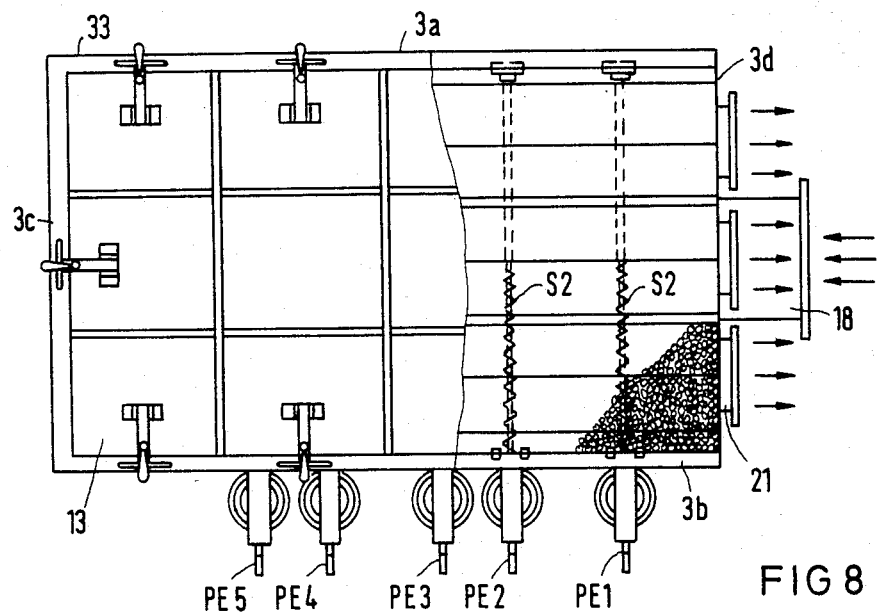
Figure 9:
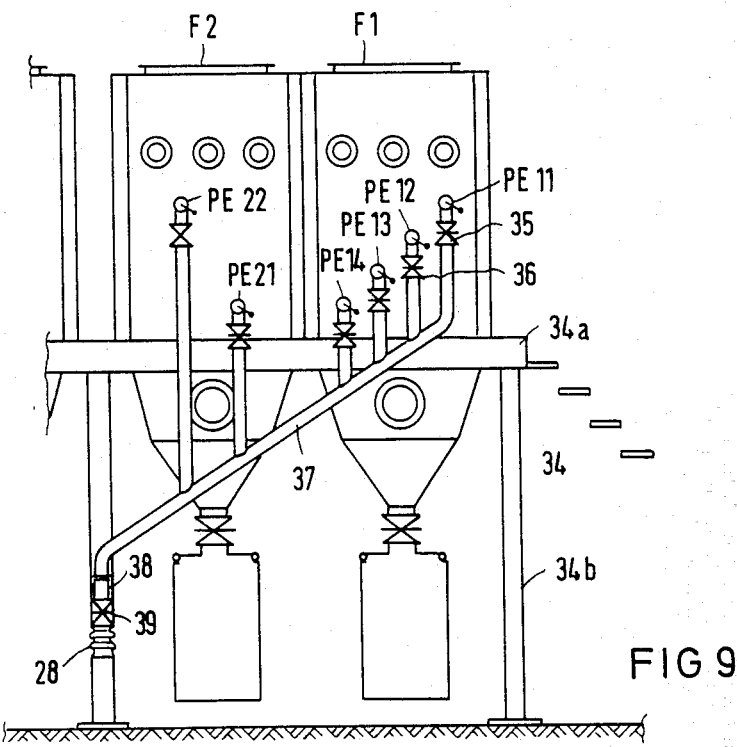

FIG. 5 is a graphical illustration of the fundamental development of the worm according to FIG. 3, in which the spiral height is plotted in millimeters on the ordinate, in dependence on the worm length and the threads per unit plotted on the abscissa, the construction of the worm to which the values in the graph relate, being shown more clearly than in FIG. 3 in a fragmentary diagrammatic view in the field of the graph;

FIGS. 6, 7 and 8 are fragmentary, partially cross-sectional and partially broken-away, front, side and plan views, respectively, of a box-shaped adsorption filter, which is equipped with five sample-taking apparatus, the sample-taking worms thereof having the fundamental development according to FIG. 3; and FIG. 9 is a fragmentary, front-elevational view, partly broken away, of several sample-taking apparatus, which are connected to two mutually adjoining filter boxes, to which a common collecting pipe with a collecting container is associated.

Referring now to the figures of the drawing in detail, and first particularly to FIG. 1 thereof, it is seen that a sample-taking apparatus, generally indicated with reference symbol PE, projects with an uncovered sample-taking worm S1 through a discharge outlet 1 of a container 3, containing bulk material feed 2, the outlet having a circular cross section. A container 3, in particular, is formed with a rectangular cross section, so that container walls 3a and 3b which are opposite each other at a distance, a rear wall 3d and an outer bracing rib 33, are provided. The container 3, for example, belongs to an adsorption filter, so that individual particles 2.1 of the bulk material feed 2 can be activated carbon substances, such as cylindrical substances from 1 to 2 mm in diameter and 1.2 to 2 mm in length, produced from extruded coal. The particles 2.1 of the bulk material feed 2, which in this case also can be characterized as a filter bed, flow through the container 3 and the threads of the sample-taking worm S1 from top to bottom, as the flow arrows indicate. This occurs, when on the bottom of the container, which is better described below according to FIG. 6, particles are discharged, and corresponding amounts of bulk material slide down from the top. In the case of an adsorption filter, particularly an activated carbon filter, the feed is contained in a quasi-stationary operation, except for the above-mentioned particle exchange. This means that particles only slide down when samples of bulk material in the partial cross section areas are taken by the sample-taking apparatus PE. In the case of the adsorption filter, the air to be cleaned flows in the normal way in the counterflow from bottom to top through the filter bed according to arrows f2; this will also be better described according to FIG. 6. However, the invention is not limited to counterflow adsorption filters, but is also generally applicable to such filters having a filter bed that flows through from gas to be cleaned in the cross flow or cross counterflow. Furthermore, in this case, the sample-taking apparatus PE with its sample-taking worm S1 would project into the filter across to the gas flow direction in a suitable way. As already described above, the invention is also to be used to advantage in the case of other bulk material feed, where sample-taking is to be carried out in the quasi-stationary condition of the feed, which results in a representative cross section of the feed, so that the desired piston flow is not disturbed.

A worm housing 4 of the sample-taking apparatus PE is provided in the form of a cylindrical hood, which penetrates the wall 3b and is fastened or welded, respectively, with a flange 4.1 at the wall region 3b, which surrounds the discharge outlet 1, and likewise at the bracing rib 33. In the area of a deflection space 4a, a worm shaft 5 penetrates the front wall 4b of the worm housing 4 in a pivot bearing 7. A motor and gear box MG is mounted or a crank handle can be fastened outside, on the front wall 4b. These elements are coupled with the worm shaft 5, but are not illustrated in a more detailed manner so that, in the direction of an arrow f3, by turning of the worm S1 in the counter clockwise direction corresponding bulk material samples can be conveyed from the feed 2 into the space 4a and from there to a collecting apparatus in FIG. 1, which is not represented in detail.

For better facility of inspection, the particles 2.1 of the feed are only partially represented, although they fill up the entire container or hopper space represented in FIG. 1, and the worm S1 is represented substantially thicker and shorter than in reality, in order for the operation to be better recognizable.

From FIGS. 1 and 2 it is clear that the developed surface of the worm threads, generally indicated with reference numeral g, has increasingly smaller conveying surfaces extending along an imaginary surface of projection normal to the worm shaft 5 with increasing depth of immersion x of the worm S1 into the feed 2. The size of the threads g depend on the spiral height of the worm threads g, which is generally indicated with reference numeral h, and it is dependent upon a position coordinate term x and the relation $h = f(x)$. The spiral height h is the distance measured from the worm core, in other words from the outer periphery of the worm shaft 5 to the outer periphery of the worm. This core is signified toward the telescoping or immersion end 8 of the screw shaft by steps in a tapering worm construction according to FIGS. 1 and 2, with reference symbols h5 to h1 respectively, as seen from the telescoping end 8 to the discharge outlet 1. The individual worm segments have reference symbols s1 to s5 as seen in the same direction, and mutually coaxial and partially concentrically formed hollow cylindrical, trunk piston-shaped bulk material, conveyed to the discharge outlet 1, is arranged in layers and has reference symbols a to e as seen from the inside to the outside. When the worm S1 is also turning in the conveying direction, first of all the hollow cylindrical segments of the particles a to e, which are found at the respective worm segments s1 to s5, are transported to the discharge outlet 1. This means that each of the worm segments s1 to s5 takes a representative bulk material sample from the feed 2 surrounding it, which is equally distributed over the worm length. This effect is ensured not only by the first worm turns, but for any number of worm turns, provided only that enough bulk material can slide down from the top. This depends on the fact that the worm segment S1 respectively conveys a trunk piston-shaped, hollow cylindrical bulk material segment a in the discharge direction f3. The worm segment s1 respectively conveys its hollow cylindrical bulk material segment b, which accumulates at the outer periphery of the bulk material segment a, etc. This conveying effect, through which hollow cylindrical bulk material segments are respectively accumulated in layers at the outer periphery from the hollow cylindrical bulk material segments with smaller peripheries, and move with them in a trunk piston-shape in the conveying direction, is illustrated through incorporating horizontal layer lines k in FIG. 1, which correspond to concentric circles k in FIG. 2. In FIG. 2, the radius of the worm shaft 5 is additionally indicated with reference symbol $r_{sa}$. When sample-taking worms of longer lengths are used it is recommended, as indicated in FIG. 1, that the telescoping end 8 of sample-taking worm S1 pivot in a pivot bearing 9, which is supported or formed of a holding rod or holding pipe 10, respectively, which, for example, is fastened with a flange 10a at the side wall 3a in alignment with the worm shaft 5. The sample-taking worm S1, according to FIG. 1, is reduced in the direction x according to a type of step-shaped curve. This has the advantage of allowing the sample-taking worm to be assembled corresponding to the desired length of individual worm segments s1 to s5 at different diameters, which are obtainable on the market, so that the central worm core or the worm shaft 5, respectively, is formed of a tie rod, on which the individual worm segments can be pushed by means of a key, gearing, or the like and can be held secure against distortion. In the axial direction, the individual worm segments can be held together through suitable non-illustrated screws.

The consistency of the sample-taking of the bulk material can be further improved through the use of an embodiment of the sample-taking worm S2 according to FIG. 3, in which the spiral height h is a constant function of x. This means that the spiral height h decreases in a constant conical tapering in the direction x toward the telescoping end 8, and that therefore, the conveying surfaces decrease accordingly. The worm core or the diameter of the worm shaft 5, respectively, is constant over the length x as in the first embodiment. The worm S2 is not right-handed like the worm S1, but is left-handed instead; therefore, the worm takes samples when the worm is turned clockwise as viewed in the direction f3. This embodiment according to FIG. 3 will incidentally be better described according to FIG.

Figure 3A:
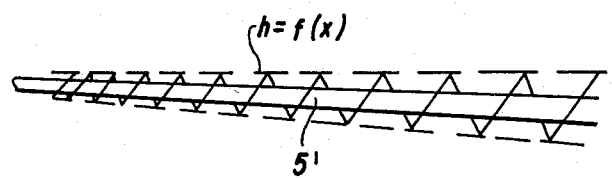
FIG. 3a is a view similar to FIG. 3, with a tapered shaft.

5. As shown in FIG. 3a, the shaft 5' is also tapered. Furthermore, reference is made to the embodiment of the sample-taking apparatus S3 according to FIG. 4 which is likewise left-handed, in which the sample-taking worm S3 has a constant outside diameter over its conveying length with respect to the coordinate x. This means that $D_S$ is constant, but its core diameter $r_{sa}$ increases from the outer worm beginning (x=0) of the bulk material up to the inner worm end 8 of the bulk material. Therefore, the spiral height h is likewise a function of the position coordinate x, meaning that the coordinate decreases as x increases, and the conveying surfaces simultaneously become smaller as well. In this way, a hollow piston-shaped, layered transport as described according to FIG. 1 also occurs. However, the hollow cylindrical layers, coming from the telescoping end, do not form the inner layers, but instead form the outer layers, and the layers closest to the discharge outlet 1 do not form the outermost, but rather form the innermost layers. However, the embodiment form according to FIG. 3 is given preference as compared to the embodiment form according to FIG. 4, while the volume of the sample-taking worm of the worm S3 according to FIG. 4 is larger than the volume of the worm S2 according to FIG. 3 for the same conveying capacity. Therefore, the principle that through the sample-taking apparatus the bulk material feed should be influenced as little as possible, is better accomplished by the construction of the worm according to FIG. 3.

Underlying the fragmentary representation of the construction of the worm section according to FIG. 5, is the concept that the right-handed sample-taking worm S2 has an outer contour, which is generally conically tapered from the discharge outlet 1 up to its telescoping end 8 (FIG. 3), and that the worm core 5 extends cylindrically. It is also possible with this embodiment for the worm shaft 5 to be likewise conically tapered toward the telescoping end. However, it is required that the tapering cone be more acute than the tapering cone of the outer worm contour, which means that it has an acute angle $0 < \alpha < \beta$, where $\alpha$ is the center or point angle of the tapering of the worm core and $\beta$ is the center or point angle of the tapering of the outer worm contour. In FIG. 5, reference numeral 11 signifies an arithmetically determined curve, which gives the spiral height in independence on the number of threads of the screw threads g and namely from the discharge end (screw thread 0g) up to the telescoping end (screw thread 10g). For the calculation, it is assumed that the sample-taking worm generates a flow of particles in an approximately axial parallel manner. This curve 11 is correct in a first approximation. However, tests have made a correction of the worm contour necessary, so that it appears like the curve 12. After that, the spiral height decreases in the direction of the position coordinate x, which extends in this case from left to right, with a nearly linearly increasing number of threads but at least in vicinity of the last three worm threads 8g to 10g, decreases over-proportionately. It has been found that the spiral height must be subjected to another correctional function, and that in vicinity of the first two worm threads from 0g to 2g be corrected in direction toward larger values, in vicinity of at least the third and fourth worm threads from 2g to 4g be corrected toward lower spiral height values, and also has a critical point at 2g. These spiral height corrections amount to a worm with a medium spiral height from 1 to 1.5 mm, merely a few millimeters, and are hardly recognizable in the fragmentary section according to FIG. 5, which tapers from left to right. Because of this spiral height correction, in the case of the sample-taking worm tested, a practically perfectly equal discharge of the filter material over the cross section of an activated carbon filter was obtained.

According to FIG. 1, it has already been described that a preferable application of the bulk material feed 2 is the case of a bulk material filter, in which fluids to be cleaned flow through and it therefore has respective inlets and outlets for the fluid on opposite filter sides, so that the sample-taking worm S1 projects generally vertically or across the fluid flow direction (arrows f2) into the feed 2, in this case into the filter bed. This is also the case in the fourth embodiment according to FIGS. 6 to 8. FIG. 6, in which equivalent parts have the same reference symbols, is explained first. In FIG. 6, the bulk material feed is an adsorption filter, especially an activated carbon filter, with a discontinuous flow from top to bottom of particles or activated carbon substances 2.1, respectively, of the adsorption means according to flow arrows f1, in this case also along the spiral of the sample-taking worm, and with a continuous flow of gases to be filtered in a counter-flow, from bottom to top according to flow arrows f2. In this case, at least one sample-taking worm S2 of a sample-taking apparatus PE projects in the horizontal direction into the filter bed 2. The adsorption filter, represented in FIGS. 6 to 8, generally includes the box-type housing or container 3 with a lockable cover 13, and a downwardly conically tapered, funnel-shaped bottom 14, which leads into a delivery socket 31, with a discharge outlet and a shutter or closure 15 of upper components 16, lower components 17 and a gas supply 18, associated therewith. The box-type filter container 3 with a rectangular cross section above the funnel-shaped bottom 14, has a side wall pair 3c, 3d (small sides), besides the two side walls 3a, 3b (longitudinal sides) as seen in FIG. 8. The adsorption means in the form of a flowable filter block particularly activated carbon substances, is generally found in the region between the lower components 17 and the cover 13, and fully fills the space between the lower components 17 and the upper components 16. The feed socket or connecting piece of the gas supply 18 is protected against downwardly falling adsorption means 2 by a peaked roof 19 and a large area sieve 20. The gas is eliminated from the filter by means of the upper components 16, which are formed of several exhaust pipes that are mutually parallel and extend from the front housing wall 3c to the back housing wall 3d. These exhaust pipes are formed of an upper roof-shaped covering 16.1 and a downwardly directed, V-shaped perforated covering 16.2, the roof edges 16.3 of the upper covering overlapping the respective downwardly directed covering. The exhaust pipes 16 are connected to collecting pipes 21, which are mounted on the back housing wall 3d with flanges that are not shown in detail. The exhaust pipes 16 at the same time form flow guide bodies for the equal distribution of the adsorption means 2, found in a storage space 22. The pipes are obviously disposed at a specific distance from each other and from the housing walls.

The adsorption means filled in from the top impinges upon the components 17 in the lower area of the container 3, by providing construction elements for carrying the adsorption means feed 2, for the equal feeding of the gas to be cleaned into an adsorption space 23 and for the equal removal of a respective spent or charged layer of the adsorption means. These components 17 are formed of louver-shaped two-piece, symmetrical roofs with a trapezoidal lower part 17.1 and a coping-shaped upper part 17.2 associated therewith, which is disposed at a vertical distance relative to the lower part 17.1. The components 17 are respectively disposed vertically below an exhaust pipe 16 and parallel to the pipe in such a manner as to result in center to center distances 17a, 17b and 17c reducing in a funnel shape, from top to bottom, analogous to the upper components and result in distances analogous to the housing walls 3a, 3b, wherein the angle of inclination of all roof slopes of the lower components 17 is approximately 45°. The downward funnel-shaped tapering gap between the lower roof-shaped components discharge by means of slides 24 and closeable longitudinal slots 17.3, into a collecting chamber 14.1 of the funnel bottom 14. The slides 24 are pivoted at a swivel axis 24.1 so as to be swingable in both directions, and are coupled together through a lever system 24.2, which can be moved by a centrally disposed drive shaft 24.3. The adsorption space 23, as well as the active zone of the filter, is defined by the distance 25 between the upper points of the lower components 17 and the lower points of the upper components 16. This distance is between 200 to 1000 mm, respectively, according to the size of the filter. It is recognizable, that in the case of the discharge of a layer of the adsorption means 2, by opening of the slides 24, the particles dropping through the slots 17.3 downward into the space 14.1, cover a certain distance in a free fall to the particles of a lower feed 2a of spent particles. This is important, in order to ensure that inside the adsorption space 23, a so-called piston flow with practically plane-parallel movement of the feed layers from top to bottom can be set up, so that corresponding layers, which are discharged at the lower side, corresponding to layers of unused adsorption substances, can flow down from the top, from an upper storage space 16a.

It can furthermore be seen from FIG. 6 that the aforementioned sample-taking apparatus PE, which in principle is constructed similarly to the apparatus according to FIG. 1, has a sample-taking worm conically tapering up to the telescoping or immersion end, analogous to FIG. 3. The dimensions and measurements correspond extensively to the true proportions, in contrast to FIG. 1 and FIG. 3; the conicity of the worm S2 is slight; it is relatively thin, while for each sample-taking relatively small amounts of a few hundred grams are taken, and because of the slenderness of the sample-taking worm, the binding or formation of the feed is only slightly influenced in its filtering property. The holding rod 10, which is mounted in the inner wall 3a with a double flange 10a, is longer than in the first embodiment according to FIG. 1, so that the sample-taking worm S2 only reaches a little more than half the filter width. However, the sample-taking worm can also be constructed to be longer and to reach practically the entire filter width. In the filter represented, the use of a rectangular cross section is especially favorable when, as shown, the sample-taking worm S2 with its shaft parallel to the shell surface, in this case the side walls 3c, 3d, of the filter container 3, projects into the filter bed 2. This is recognizable and especially clear in FIG. 8, which in connection with FIG. 7 shows that in the illustrated embodiment, five sample-taking worms S2, which belong to corresponding individual sample-taking apparatus PE 1 to PE 5, is disposed at a surface (side wall 3b) of the filter container 3 on different levels z1 to z5 in height and laterally according to y-coordinates y1 to y5 displaced relative to each other. Therefore, in FIG. 6 the highest sample-taking apparatus PE 1 is represented. The numbers of the sample-taking apparatus PE depend on the filter size; to receive a rather reliable indication of the loading condition, at least two sample-taking apparatus should be used in an advantageous manner, which are staggered in height and laterally to each other. The distinguishable sloping formation of at least three sample-taking worms S2 in FIG. 7, five being represented, has the advantage of permitting a view of the condition inside of the entire filter height and also over the condition along the y-coordinate, in other words across it. The y-z system of coordinates belonging thereto is shown in FIG. 7.

FIG. 6 likewise shows the worm end, which projects outside through the container wall 3b and is surrounded by the worm pipe 4, to which a collecting apparatus for the filter samples that have been taken, is connected. This collecting apparatus A1 includes a sluice, especially having a slight glass-shaped sluice container 26 and shut off devices 26a and 26b, which are connected upstream and downstream, and a discharge pipe 27 connected to the sluice with a collecting container 28. The discharge pipe 27 ends in a fluted protective bag ring 29, at which a special protective bag formed of a transparent plastic as a collecting container 28, is clamped gas-tight with the rim of its opening. Plug valves or sluice valves can serve as shut off devices 16a and 26b. These valves are provided with a rocking lever for manual operation, as shown. However, remote operation through servo motors connected thereto can also be provided. This feature also applies for the crank 30 for the turning of the worm S2. This crank can also be replaced by a motor gear unit MG according to FIG. 1, for the purpose of the remote operation.

A collecting apparatus A1 to A5 is assigned to each of the sample-taking apparatus PE1 to PE5 as seen in FIG. 7. For better clarity the collecting apparatus A2 to A4 are not represented. The discharge pipe 31 of the filter container 3 also discharges in a suitable manner through the closure 15, particularly a swivel damper closure, and through a protective bag flange ring 31a into a protective bag 32, which is clamped gas-tight to the ring 31a.

From FIGS. 6 to 8 it is seen that the filter container 3 with its side walls 3a to 3d is still reinforced by reinforcing ribs 33. These reinforcing ribs 33 have a mechanical purpose; they serve to reinforce and fasten the cover locking devices 13a. A pyramidal wall apron extension 33a disposed in the lower part of the box, can serve as a so-called standing frame, in other words surfaces 33a1 thereof serve as supports for the filter container.

In the case of the embodiment according to FIG. 9 two adjoining filters or filter containers F1, F2, respectively, are shown, which are generally constructed as described in the case of the fourth embodiment according to FIGS. 6 to 8. The filters rest on a supporting frame, formed of horizontal supporting beams 34a and vertical columns 34b. The sample-taking apparatus PE 11 to PE 14 of the filter F1 are disposed similarly to FIG. 7, staggered in height and laterally to each other, and likewise for the sample-taking apparatus PE 21, PE 22 of the filter 2.

Nevertheless, each sample-taking apparatus does not have its own sluice, but several discharge pipes 36 are respectively connected to a sample-taking worm downstream of shut off devices 35, which discharge in common, with an inclined collecting pipe 37, which again discharges through a sight glass extension 38 and a second shut off device 39 into the protective bag 28, which is clamped gas-tight to the collecting pipe end. Therefore, for each sample-taking apparatus a shut off device is omitted. However, the samples then must be taken one after another timely, so that a mixture of the samples does not occur. This construction of the collecting apparatus can be effective not only for a single filter F1, but for several adjoining filters; in FIG. 9 this counts for the two filters F1, F2.

The material used for the sample-taking worms S1, S2, S3 is a special corrosion-resistant fine steel alloy, which is likewise used for the upper and lower components 16, 17 of the filter 3. Furthermore, the inner surfaces of the container 3, which are exposed to the filter substances 2, 2.1, are advantageously corrosion-resistant.

I claim:

1. Sample-taking apparatus, comprising a container for bulk material feed, said container having an upper cover region, a lower discharge region and a side wall having a discharge opening formed therein, the bulk material feed flowing at least discontinuously from said upper cover region to said lower discharge region of said container, an exposed sample-taking worm being attached to said side wall and projecting through said discharge opening into the feed for conveying bulk material samples from the feed by rotating, a rotary drive connected to said sample-taking worm, and a collecting device integral with said container, said worm having a shaft with an end, at least said end being immersed in the feed, said worm having worm threads formed thereon with surfaces forming an imaginary surface of projection extended normal to said worm shaft, said worm thread surfaces forming worm segments with increasingly smaller conveying surfaces as seen in direction toward increasing depth of immersion of said worm into the feed, during sample-taking in a quasi-stationary condition of the feed, said worm threads accumulating layered hollow cylindrical bulk material segments between said worm threads in subsets corresponding to worm segments from any of said worm threads having a given spiral height to an adjacent one of said worm threads having a larger spiral height as seen in direction from said end of said shaft to said discharge opening, said subsets being representative of the bulk material of said respective segments of said worm, the bulk material feed being a bed of a bulk material filter, through which fluids to be cleaned flow in a given direction, the filter bed having respective feeding and discharge filter sides, said sample-taking worm projecting into the filter bed substantially perpendicularly to the fluid flow direction.

2. Sample-taking apparatus according to claim 1, wherein said conveying surfaces of said worm segments steadily decrease in size as seen in direction toward increasing depth of immersion of said worm into the feed.

3. Sample-taking apparatus according to claim 1, wherein said sample-taking worm has a substantially conically tapered outer contour from said discharge opening to said end of said shaft, and said shaft is cylindrical.

4. Sample-taking apparatus according to claim 1, wherein said sample-taking worm has a substantially conically tapered outer contour from said discharge opening to said end of said shaft, and said shaft is also conically tapered toward said end of said shaft and is more pointed than said outer contour of said worm.

5. Sample-taking apparatus according to claim 1, wherein said spiral height of said worm threads from said shaft to the outer periphery of said worm determining the size of said respective conveying surfaces, decreases substantially linearly as seen in direction toward said shaft end along said shaft.

6. Sample-taking apparatus according to claim 5, wherein the three smallest of said spiral heights of said worm threads are decreased over-proportionately as compared to the others of said worm threads.

7. Sample-taking apparatus according to claim 5, wherein the spiral height of the worm threads is increased in vicinity of the first two threads toward said discharge opening and is decreased in vicinity of the third and fourth threads.

8. Sample-taking apparatus according to claim 1, wherein the bulk material feed is an adsorption filter with a discontinuous flow of adsorption means from top to bottom and with a continuous counter flow of gases to be filtered from the bottom to the top, said sample-taking worm projecting in the horizontal direction into the filter bed.

9. Sample-taking apparatus according to claim 1, wherein the bulk material filter has a substantially rectangular cross section, said container has surfaces, and said sample-taking worm projects into the filter bed with said shaft being parallel to said surfaces of said container.

10. Sample-taking apparatus according to claim 8, wherein the bulk material filter has a substantially rectangular cross section, said container has surfaces, and said sample-taking worm projects into the filter bed with said shaft being parallel to said surfaces of said container.

11. Sample-taking apparatus according to claim 9, including at least one additional sample-taking worm, at least two of said worms being disposed at one of said surfaces of said container at different heights relative to the bulk material filter and laterally staggered with respect to each other.

12. Sample-taking apparatus according to claim 11, wherein said sample-taking worms include at least three sloping worms.

13. Sample-taking apparatus according to claim 8, wherein said shaft has another end projecting outside said container wall, and including a worm tube disposed on said other end and a collecting device connected to said worm tube, said collecting device including a sluice having a sluice pot, shut-off device connected upstream and downstream of said sluice pot, a discharge pipe connected to said sluice, and a collecting container connected to said discharge pipe.

14. Sample-taking apparatus according to claim 13, wherein said collecting container is a protective bag having an opening formed therein defining a rim, and including a fluted protective bag ring at which said discharge pipe terminates, said ring being gas-tightly clamped to said rim.

15. Sample-taking apparatus according to claim 11, including first shut-off devices respectively connected to a plurality of said sample-taking worms, discharge pipes respectively connected downstream of said first shut-off devices, a common inclined collecting pipe into which said discharge pipes are connected for discharging, a sight glass extension connected to said common collecting pipe, a second shut-off device connected to said sight glass extension, and a protective bag gas-tightly clamped to said collecting pipe through said extension and second shut-off device.

16. Sample-taking apparatus according to claim 15, including at least one additional container having sample-taking worms and discharge pipes, said discharge pipes of said sample-taking worms of at least two mutually adjoining containers being connected to collecting pipes.

17. Sample-taking apparatus according to claim 1, including a worm tube disposed on said worm at an end of said shaft opposite said first-mentioned end, a support rod fastened to said container wall opposite said worm tube, and a pivot bearing being supported by said support rod and being in alignment with and pivotably connected to said first-mentioned end of said shaft.

18. Sample-taking apparatus according to claim 1, wherein said sample-taking worm has a constant outer diameter throughout the length thereof, and said shaft has a diameter being increased as seen in direction from said discharge opening to said end of said shaft.

19. Sample-taking apparatus, comprising a container for bulk material feed, said container having an upper cover region, a lower discharge region and a side wall having a discharging opening formed therein, the bulk material feed flowing at least discontinuously from said upper cover region to said lower discharge region of said container, an exposed sample-taking worm being attached to said side wall and projecting through said discharge opening into the feed for conveying bulk material samples from the feed by rotating, a rotary drive connected to said sample-taking worm, and a collecting device integral with said container, said worm having a shaft with an end, at least said end being immersed in the feed, said worm having worm threads formed thereon with surfaces forming an imaginary surface of projection extended normal to said worm shaft, said worm thread surfaces forming worm segments with increasingly smaller conveying surfaces as seen in direction toward increasing depth of immersion of said worm into the feed, during sample-taking in a quasi-stationary condition of the feed, said worm threads accumulating layered hollow cylindrical bulk material segments between said worm threads in subsets corresponding to worm segments from any one of said worm threads having a given spiral height to an adjacent one of said worm threads having a larger spiral height as seen in direction from said end of said shaft to said discharge opening, said subsets being representative of the bulk material of said respective segments of said worm, the size of said conveying surfaces and said spiral height of said threads of said worm decreasing as seen in direction toward increasing immersion of said worm in the feed, according to a type of step curve.

20. Sample-taking apparatus according to claim 1, wherein the bulk material feed is an adsorption filter with a discontinuous flow of adsorption means from top to bottom and with a continuous counter flow of gases to be filtered in a given direction through the filter bed, said sample-taking worm projecting into the filter bed across said gas flow direction.

* * * * *